United States Patent [19]

Wehrli

[11] B  4,072,723
[45]  Feb. 7, 1978

[54] PREPARATION OF 2,3,6-TRI-LOWER ALKYL PHENOLS

[75] Inventor: Pius Anton Wehrli, Verona, N.J.

[73] Assignee: Hoffmann-La Roche Inc., Nutley, N.J.

[21] Appl. No.: 501,128

[22] Filed: Aug. 28, 1974

[44] Published under the second Trial Voluntary Protest Program on February 24, 1976 as document No. B 501,128.

Related U.S. Application Data

[62] Division of Ser. No. 260,024, June 2, 1972, Pat. No. 3,857,892, which is a division of Ser. No. 805,365, March 7, 1969, Pat. No. 3,692,839.

[51] Int. Cl.² ............................................. C07C 39/06
[52] U.S. Cl. ............................ 260/621 H; 260/624 C
[58] Field of Search ................. 260/621 H, 624 R, 24, 260/624 C, 621 R; 805/365

[56] References Cited

U.S. PATENT DOCUMENTS

| 2,503,641 | 4/1950 | Taylor | 260/621 H |
| 2,640,084 | 5/1953 | Chitwood et al. | 260/621 H |
| 2,708,208 | 5/1955 | Furman | 260/621 H |

*Primary Examiner*—James O. Thomas, Jr.
*Assistant Examiner*—W. B. Lone
*Attorney, Agent, or Firm*—Samuel L. Welt; Bernard S. Leon; George W. Johnston

[57] ABSTRACT

Preparation of 2,3,6-tri-lower alkyl phenols from the condensation product of an α,β-unsaturated aldehyde with a dilower alkyl ketone.

1 Claim, No Drawings

PREPARATION OF 2,3,6-TRI-LOWER ALKYL PHENOLS

CROSS REFERENCE TO RELATED APPLICATION

This application is a division of U.S. patent application Ser. No. 260,024, filed June 2, 1972, now U.S. Pat. No. 3,857,892, which in turn is a division of U.S. patent application Ser. No. 805,365, filed Mar. 7, 1969, now U.S. Pat. No. 3,692,839.

BACKGROUND OF THE INVENTION

The commercially available 2,3,6-tri-lower alkyl phenols which are important starting materials in the synthesis of tri-lower alkyl hydroquinones, intermediates for vitamin E, are of a very low purity. This has proven extremely disadvantageous since the tri-lower alkyl hydroquinones, which are intermediates for vitamin E and related compounds, should have a high degree of purity. The alkyl hydroquinones which are prepared from the commercially available 2,3,6-tri-lower alkyl phenols generally contain impurities which result from utilizing these impure phenols as starting materials. It is with considerable difficulty and expense that the final tri-lower alkyl hydroquinones are purified for commercial use. Therefore, a method whereby 2,3,6-tri-lower alkyl phenols of high purity can be prepared from economic starting materials has long been desired in the art.

SUMMARY OF THE INVENTION

In accordance with this invention, 2,3,6-tri-lower alkyl phenols of the formula:

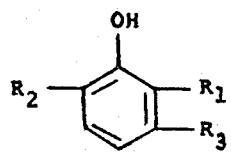

I wherein $R_1$, $R_2$ and $R_3$ are lower alkyl are prepared through the reaction of an $\alpha,\beta$-unsaturated aldehyde of the formula

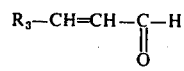

II wherein $R_3$ is lower alkyl with a ketone of the formula

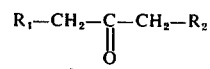

III wherein $R_1$ and $R_2$ are lower alkyl.

In this manner a simple and economic means is provided for producing pure 2,3,6-tri-lower alkyl phenols.

DETAILED DESCRIPTION

The term "lower alkyl" as used throughout the specification designates both straight and branched chain alkyl groups containing from 1 to 7 carbon atoms such as methyl, ethyl, propyl and isopropyl. The term "halogen" as used throughout the specification includes all four halogens, i.e., chlorine, fluorine, bromine and iodine with chlorine and bromine being preferred.

In accordance with a preferred embodiment of this invention, in the compounds of the formulae I, II and III, $R_1$, $R_2$ and $R_3$ are all methyl, thereby producing 2,3,6-trimethylphenol utilized in the preparation of vitamin E.

In accordance with this invention the compound of formula I is prepared via the following reaction scheme:

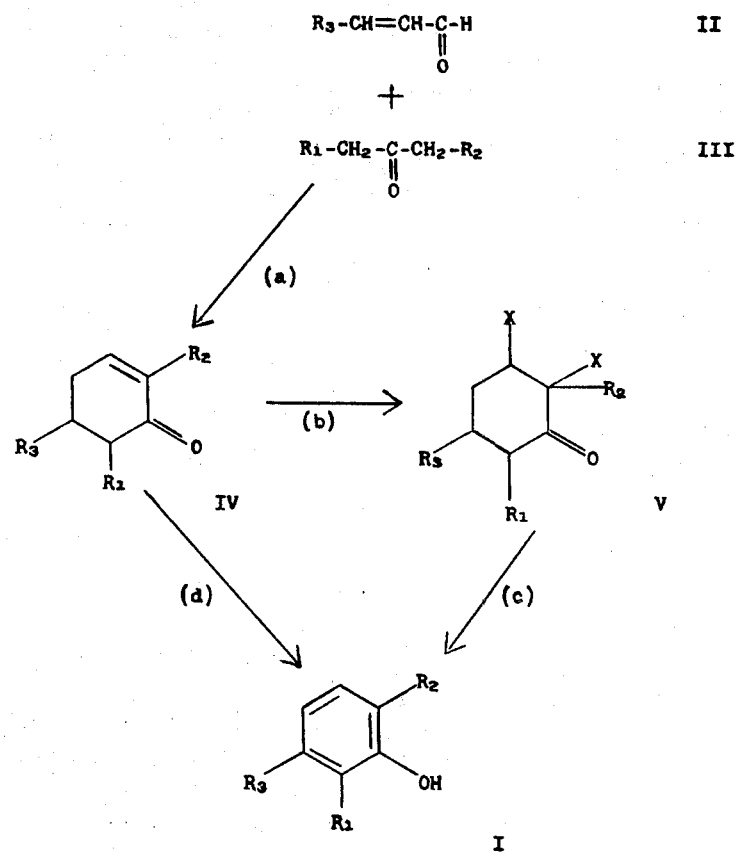

wherein $R_1$, $R_2$ and $R_3$ are as above and X is halogen.

In accordance with the process of this invention, the aldehyde of formula II is condensed with the ketone of formula III via reaction step (a) to produce the compound of formula IV above. This condensation reaction is carried out in the presence of a base. Any conventional organic or inorganic base can be utilized in this reaction. Among the conventional bases which can be utilized in carrying out this reaction are included the alkali metal hydroxides such as sodium hydroxide, potassium hydroxide, etc.; alkali metal-lower alkoxides such as sodium methoxide, sodium ethoxide, etc.; alkali metal hydrides such as sodium hydride, lithium hydride, etc.; alkali metal amides such as sodium amide, potassium amide, etc., and organic amine bases such as pyridine, piperidine, etc. In carrying out this reaction, one mole of the compound of formula II is reacted with one mole of the compound of formula III above. Generally, it is preferable that the ketone of formula III above be present in excess of the stoichiometric amount required to react with the compound of formula II above. Generally, it is preferred to have at least 5 moles of the ketone of formula III above per mole of the compound of formula II. In carrying out this reaction excess ketone of formula III above can be utilized as the reaction medium. If desired, any conventional inert organic solvent can be used as the reaction medium. Among the conventional inert organic solvents which can be utilized, toluene, benzene, xylene, dioxane, diethyl ether and tetrahydrofuran are preferred. In carrying out this reaction, temperature and pressure are not critical and this reaction can be carried out at room temperature and atmospheric pressure. However, if desired, elevated or reduced temperatures, i.e., temperatures between 10° to 100°C., depending upon the reflux temperature of the solvent medium, can be utilized.

In the next step of the process of this invention the compound of formula IV above is converted to the compound of formula V above via reaction step (b). This reaction is carried out by treating the compound of formula IV above with a halogenating agent. Any conventional halogenating agent can be utilized in carrying out the reaction of step (b). Among the conventional halogenating agents which can be utilized are included N-bromo-succinimide, alkali metal hypohalites or a halogen such as chlorine, bromine, or iodine. Generally, this reaction is carried out in an inert organic solvent. Any conventional inert organic solvent can be utilized in carrying out this reaction. Among the preferred inert organic solvents which can be utilized in carrying out this reaction are included hydrocarbons such as xylene, toluene and halogenated hydrocarbons such as carbon tetrachloride, methylene chloride, chlorobenzene, etc. Generally, this reaction is carried out by treating the compound of formula IV above with a halogenating agent at a temperature of from about 0° to −40°C.

The compound of formula V above is converted to the compound of formula I above via reaction step (c) by treating the compound of formula V above with a base or a metal selected from the group consisting of Group III metals and transition metals. Any conventional base can be utilized. Among the preferred bases are included inorganic bases such as sodium hydroxide, potassium hydroxide; and organic amine bases such as piperazine, pyridine, picoline, piperidine, etc. Any conventional Group III metal or transition metal can be utilized in carrying out this reaction. Among the preferred metals are included iron, zinc, copper, aluminum, platinum, palladium, etc. When a metal is utilized in carrying out this reaction the compound of formula V above is treated with the metal in powdered form. This reaction can take place in the presence of a conventional inert organic solvent. Any conventional inert organic solvent can be utilized. Among the conventional inert organic solvents which can be utilized are the hydrocarbon solvents such as tetralin, toluene, xylene, etc. In carrying out this reaction, temperature and pressure are not critical and this reaction can be carried out at room temperature and atmospheric pressure. However, elevated temperatures and pressures can be utilized in carrying out this reaction. If desired, the reaction can take place at conditions of temperature and pressure where the compound of formula V is in the vapor phase. Generally, it is preferred to carry out this reaction at the reflux temperature of the solvent medium.

In accordance with another embodiment of this invention, the compound of formula IV above is directly converted to the compound of formula I above, via reaction step (d) by treating the compound of formula IV above with a dehydrogenating agent. In carrying out this reaction, any conventional dehydrogenating agent can be utilized. Among the conventional dehydrogenating agents which can be utilized, dichlorodicyanoquinone, mercuric acetate and palladium on carbon are preferred. Generally, this reaction is carried out in a conventional inert organic solvent. Any conventional inert organic solvent can be utilized. Among the conventional inert organic solvents that can be utilized in this reaction, tetralin, benzene, toluene, xylene and organic acids which include lower alkanoic acids such as acetic acid are preferred. When palladium on carbon is utilized as the dehydrogenating agent, no solvent need be present and the reaction can be carried out by heating the reaction medium in the presence of air to a temperature of from about 150° to about 300°C. When a solvent is utilized, the reaction proceeds very slowly at room temperature. Therefore, it is generally preferred to utilize elevated temperatures in carrying out this reaction. In general, temperatures of from about 50° to 200°C. are preferred depending upon the reflux temperature of the solvent utilized in the reaction medium.

The invention will be more fully understood from the specific examples which follow. These examples are intended to illustrate the invention and are not to be construed as limitative thereof. The temperatures utilized in these examples are in degrees Centigrade.

EXAMPLE 1

2,5,6-trimethyl-2-cyclohexenone

Into a 250 cc 3-necked round bottomed flask, equipped with a thermometer, magnetic stirrer, drying tube and adding funnel, were placed 24 g. (0.2 m) potassium butoxide and 20 cc methanol (with ice bath cooling). 70 g. (0.8 m) 3-pentanone were added. 56.0 g. (0.8 m) crotonaldehyde dissolved in 70 g. (0.8 m) 3-pentanone were added to the stirred reaction mixture over a period of 45 minutes (the temperature was maintained between 20° and 25°). When one-third of the solution was left, 18 g. (0.15 m) more of potassium butoxide were added to the flask and the addition was continued. After completion of addition, the ice bath was removed and the reaction mixture stirred for further 30 minutes.

The reaction mixture was then partitioned between etheraqueous NaCl. The ether phase was washed 5 times with aqueous NaCl (until the aqueous wash was no longer basic to pH paper). It was dried over anhydrous sodium sulfate and concentrated at atmospheric pressure (on steam bath) until the temperature rose to 85°. The residue was then distilled under vacuum by a water pump. From the residue one obtained 2,5,6-trimethyl-2-cyclohexenone as a fraction.

EXAMPLE 2

2,3,6-trimethylphenol 13.8 g. (0.1 m) 2,5,6-trimethyl-2-cyclohexenone and 0.5 g. 5 percent Pd/C were stirred at 200° for 150 minutes in an open vessel. At the end of this time, a UV spectrum run on an aliquot showed no starting material present. The reaction mixture was filtered and partitioned between aqueous NaOH and ether. The basic phase on treatment with ice and concentrated HCl gave 2,3,6-trimethylphenol.

Additional 2,3,6-trimethylphenol was obtained from concentrating the ether phase.

EXAMPLE 3

2,3-dichloro-2,5,6-trimethylcyclohexanone 13.8 g. (10 mmoles) of 2,5,6-trimethyl-2-cyclohexenone were diluted with 50 cc of carbon tetrachloride and cooled to −20°C. At this temperature, 7.1 g. (10 mmoles) of chlorine was slowly introduced by way of a subsurface glass-tubing gas-inlet. After all of the chlorine has been absorbed, the solvent was removed under reduced pressure at 20°C. to provide 20.9 g. (100 percent of theory) of 2,3-dichloro-2,5,6-trimethylcyclohexanone as residue. This product showed a new strong band in the IR-spectrum at 1720 cm$^{-1}$.

EXAMPLE 4

7.7 g. of 2,3-dichloro-2,5,6-trimethylcyclohexanone were added to 23.1 g. of pyridine and refluxed for 6 hours. The brown reaction mixture was diluted with water, cooled in an ice bath and concentrated HCl added until strongly acidic. After three extractions with ether and two washings with saturated NaCl-solution, the organic layers were combined and dried over magnesium sulfate. After filtration, removal of the solvent and distillation of the residue (b.p. ca 120°C./11 mg Hg) one obtained 4.35 g. of 2,3,6-trimethylphenol. The IR-spectrum of this material was superimposable with an authentic sample.

I claim:

1. A process of producing a hydroxy compound of the formula:

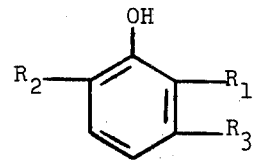

wherein $R_1$, $R_2$ and $R_3$ are lower alkyl; comprising treating a dihalo compound of the formula:

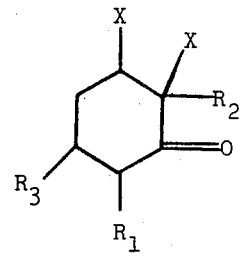

wherein $R_1$, $R_2$, and $R_3$ are as above and X is a halogen; with a base selected from the group consisting of sodium hydroxide, potassium hydroxide, pyridine, piperidine, piperazine, picoline, or a metal selected from the group consisting of zinc, copper, iron, aluminum, and platinum; said treatment being conducted in an inert organic solvent and at a temperature of from room temperature to the reflux temperature of the solvent.

* * * * *